United States Patent [19]

Leifeld

[11] Patent Number: 5,615,453
[45] Date of Patent: Apr. 1, 1997

[54] SLIVER GUIDING AND MEASURING ASSEMBLY HAVING AN EXCHANGEABLE COMPONENT

[75] Inventor: Ferdinand Leifeld, Kempen, Germany

[73] Assignee: Trützschler GmbH & Co. KG, Mönchengladbach, Germany

[21] Appl. No.: 549,312

[22] Filed: Oct. 27, 1995

[30] Foreign Application Priority Data

Oct. 31, 1994 [DE] Germany ............... 44 38 882.9

[51] Int. Cl.$^6$ .................. D01G 15/64; D01H 5/72
[52] U.S. Cl. ........................... 19/288; 19/0.23
[58] Field of Search ............... 19/0.23, 106 R, 19/236, 239, 240, 243, 287, 288, 291, 292, 150, 157; 73/159, 160

[56] References Cited

FOREIGN PATENT DOCUMENTS

| | | |
|---|---|---|
| 932088 | 8/1955 | Germany . |
| 3036697 | 4/1981 | Germany . |
| 287537 | 10/1983 | Germany . |
| 3807582 | 9/1989 | Germany . |
| 3834110 | 4/1990 | Germany . |
| 4012551 | 6/1991 | Germany . |
| 4404326 | 10/1994 | Germany . |
| 635373 | 3/1983 | Switzerland . |
| 2277106 | 10/1994 | United Kingdom . |
| 91/16595 | 10/1991 | WIPO . |

*Primary Examiner*—Michael A. Neas
*Attorney, Agent, or Firm*—Spencer & Frank

[57] ABSTRACT

An apparatus for measuring sliver thickness in a drawing frame includes first and second selectively used sliver guiding devices having converging inner wall faces for bringing a plurality of simultaneously introduced slivers together to form a sliver assembly constituted by side-by-side positioned running slivers arranged in a plane. Each sliver guiding device has a sliver inlet and a smaller sliver outlet. Either the inlet or the outlet, or both, have different passage areas in the different sliver guiding devices. A receiving arrangement accommodates the selected sliver guiding device in the apparatus. The apparatus further includes a sensor element and a counterelement laterally contacting the sliver assembly from opposite sides. The sensor element is urged into a resilient contact with the sliver assembly whereby the sensor element undergoes excursions upon variation of thickness of the sliver assembly. The sensor element and the counterelement together define a constriction through which the sliver assembly passes. A transducer converts excursions of the sensor element into electric pulses. A withdrawing roller pair supported downstream of the sliver guiding device pulls the sliver assembly through the sliver guiding device.

4 Claims, 6 Drawing Sheets

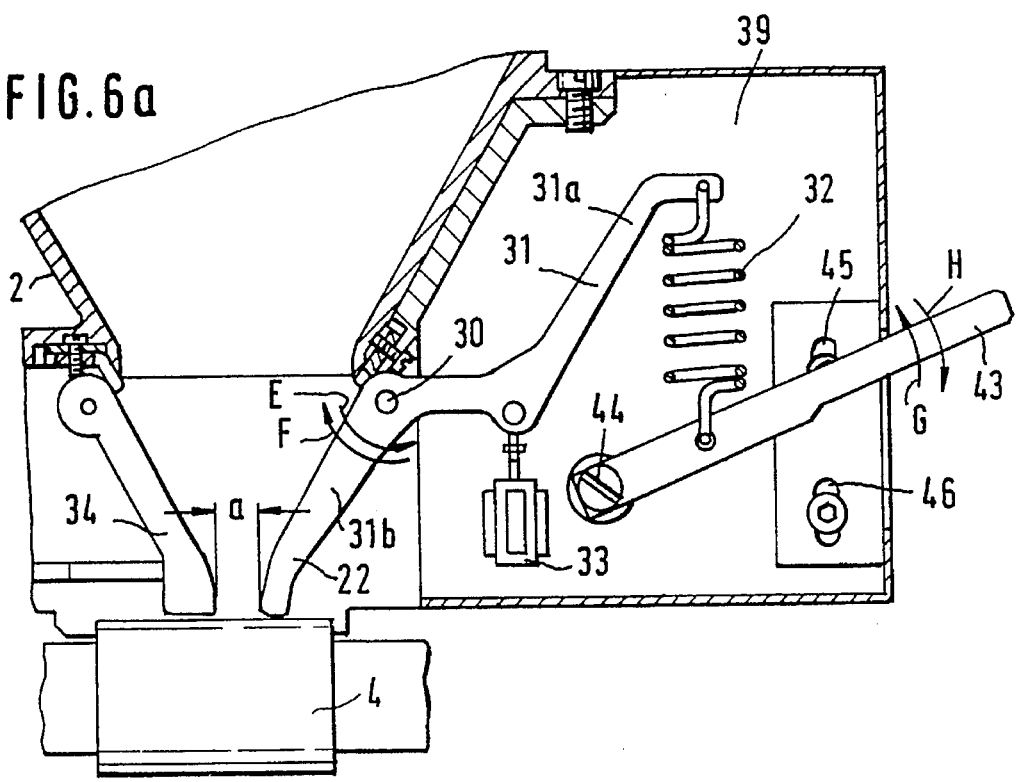
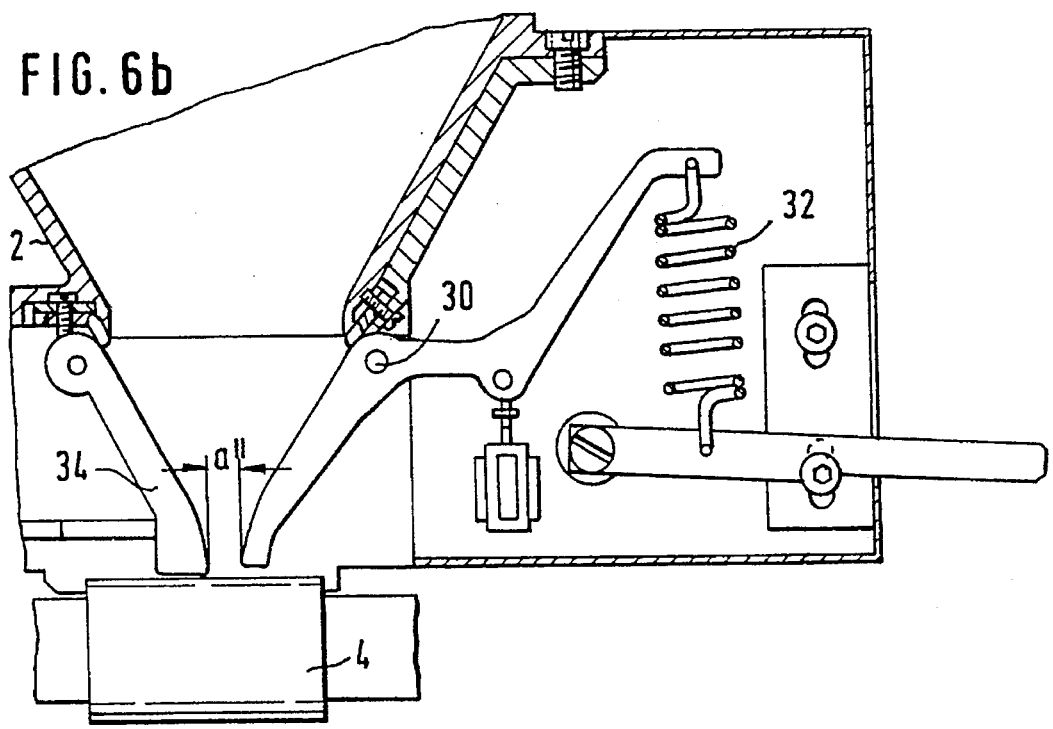

SLIVER GUIDING AND MEASURING ASSEMBLY HAVING AN EXCHANGEABLE COMPONENT

CROSS REFERENCE TO RELATED APPLICATION

This application claims the priority of German Application No. P 44 38 882.9 filed Oct. 31, 1994.

BACKGROUND OF THE INVENTION

This invention relates to a sliver guiding assembly for guiding simultaneously running slivers and sensing the sliver thickness in a drawing frame, for example, a regulated drawing frame. The assembly which is arranged at the inlet of the drawing frame includes a sliver guiding device having at least two oppositely located converging walls which bring together the simultaneously introduced slivers to form a sliver assembly in which the individual slivers are in a lateral contact with one another and lie in a single plane. The sliver guiding assembly further has a withdrawing roller pair which is situated downstream of the sliver guiding device and through which the sliver assembly passes and thereafter the individual slivers assume a divergent orientation. The sliver guiding device is associated with a biased, movable sensor element which cooperates with an operationally stationary countersurface and defines therewith a constriction for the sliver assembly. The sensor element changes its position as the thickness of the sliver assembly varies and the excursions of the sensor element are converted into control pulses.

In a known arrangement a sliver guiding device is provided which has two lateral components as well a lid component. The underside of the sliver guiding device is formed by a fiber processing arrangement. A change in the position of the lateral components of the sliver guiding device is made possible by adjustment via slots and set-screws. The lateral components are thus slidable for adjustment along the slots in a direction towards and away from one another. It is a disadvantage of this prior art arrangement that between the upper and lower edges of the lateral walls and the lid component or base component, fibers may be caught which may lead to operational disturbances. Furthermore, the angle which the lateral walls of the sliver guiding device form with one another always remains the same.

SUMMARY OF THE INVENTION

It is an object of the invention to provide an improved apparatus of the above-outlined type from which the discussed disadvantages are eliminated, which makes possible a disturbance-free operation and also allows an adjustment of the angle which the lateral surfaces of the sliver guiding device form with one another.

This object and others to become apparent as the specification progresses, are accomplished by the invention, according to which, briefly stated, the apparatus for measuring sliver thickness in a drawing frame includes first and second selectively used sliver guiding devices having converging inner wall faces for bringing a plurality of simultaneously introduced slivers together to form a sliver assembly constituted by side-by-side positioned running slivers arranged in a plane. Each sliver guiding device has a sliver inlet and a smaller sliver outlet. Either the inlet or the outlet, or both, have different passage areas in the different sliver guiding devices. A receiving arrangement accommodates the selected sliver guiding device in the apparatus. The apparatus further includes a sensor element and a counterelement laterally contacting the sliver assembly from opposite sides. The sensor element is urged into a resilient contact with the sliver assembly whereby the sensor element undergoes excursions upon variation of thickness of the sliver assembly. The sensor element and the counterelement together define a constriction through which the sliver assembly passes. A transducer converts excursions of the sensor element into electric pulses. A withdrawing roller pair supported downstream of the sliver guiding device pulls the sliver assembly through the sliver guiding device.

By virtue of the fact that the entire sliver guiding device is replaceable in the sliver guiding and sensing unit, the fibers can unimpededly flow therethrough and thus the arrangement is devoid of components, corners or angles where the fibers may be caught. The sliver guiding devices of different dimensions are one-piece components, that is, the lateral walls as well as the lid or bottom wall form a closed rigid unit. Further, an exchange of the sliver guiding devices results in an improved adaptation since the angle formed between the lateral faces is also different. The sliver guiding assembly according to the invention thus permits in a simple and advantageous manner an improved guidance in case the type or number of slivers is altered.

BRIEF DESCRIPTION OF THE DRAWING

FIG. 4a is an enlarged top plan view of a detail of FIG. 3a.

FIGS. 6a and 6b are sectional top plan views of another preferred structural embodiment of the invention, showing two different operational positions.

DESCRIPTION OF THE PREFERRED EMBODIMENTS

Figure 1A:
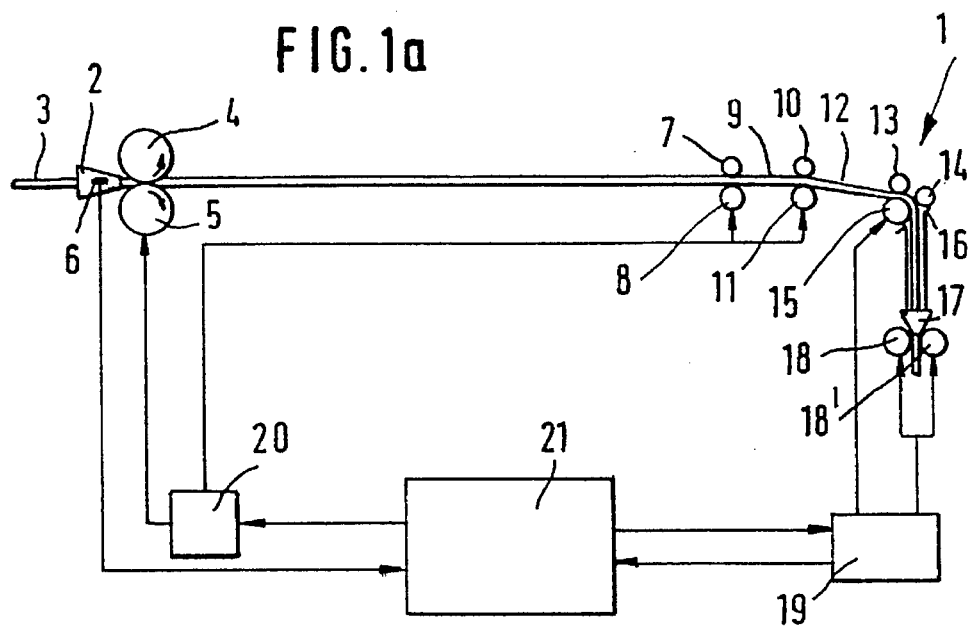
FIG. 1a is a schematic side elevational view, with block diagram, of a regulated drawing frame, incorporating the invention.

FIG. 1a illustrates a high production drawing frame which may be, for example, an HS 900 model, manufactured by Trützschler GmbH & Co. KG, Mönchengladbach, Germany. A plurality of slivers 3, paid out from non-illustrated coiler cans, enter a sliver guiding device 2, through which they are drawn and further advanced by a pair of cooperating withdrawing rollers 4 and 5. In their travel through the sliver guiding device, the slivers 3 move past a measuring member 6. The drawing frame 1 includes an upper inlet roller 7 and a lower inlet roller 8 which are associated with the pre-drawing zone 9 delimited at the downstream end by the upper predrawing roller 10 and the lower predrawing roller 11. Between the roller pair 10, 11 as well as a roller pair formed of the upper main drawing roller 13 and the lower main drawing roller 15 the main drawing zone 12 extends. The lower main drawing roller 15 is associated with a second upper main drawing roller 14. Such an arrangement is referred to as a four over three drawing system.

The drafted slivers 3, after passing through the roller pair 14, 15, reach the inlet of a sliver guide 16 and are drawn through a sliver trumpet 17 arranged at the downstream end of the sliver guide 16 by cooperating delivery rolls 18, 18'. In the sliver trumpet 17 the slivers are combined into a single sliver deposited into a non-illustrated coiler can. The main drawing rollers 13, 14, 15 and the delivery rollers 18, 18' are driven by a main motor 19 controlled by a computer 21. The signals generated by the measuring member 6 at the sliver guiding device 2 are applied to the computer 21 and are converted into control signals which are applied to a regulating motor driving the withdrawing rollers 4, 5 as well as the rollers 7, 8, 10 and 11 of the pre-drawing zone 9. According to the signals of the measuring unit 6, representing the fluctuating thickness values of the sliver assembly formed of the slivers 3, the computer 21 sends control signals to the regulating motor 20 which accordingly varies the rpm's of the rollers 4, 5, 7, 8, 10 and 11.

Figure 1B:
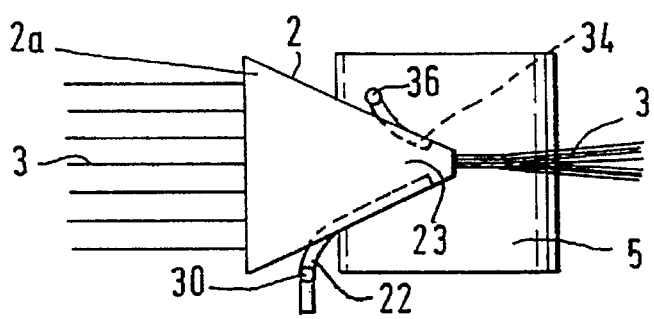
FIG. 1b is an enlarged top plan view of a component illustrated in FIG. 1a, showing further details.

Turning to FIG. 1b, in the top plan view illustrated therein the upper withdrawing roller 4 is not shown for clarity. The slivers 3 are brought together in the sliver guiding device 2 to form the sliver assembly in which the individual slivers are in a mutually contacting relationship and extend in a single plane. The measuring unit 6 symbolically shown in FIG. 1a includes a sensor element 22 which is rotatably supported by a bearing 30 for swinging motions in a direction parallel to the single plane in which the slivers 3 of the sliver assembly lie. The structure and function of the sensor element 22 will be described later.

Opposite the sensor element 22 a counterelement 34 is provided which is adjustable to vary, in cooperation with the sensor element 22, the passage width of a constriction 23 at the outlet end of the sliver guiding device 2. As will be described later, the counterelement 34 is adjustable by swinging it about a pivot 36 in a direction parallel to the single plane in which the slivers 3 of the sliver assembly lie. The counterelement 34 may be immobilized in its adjusted position, as will also be described later.

Figure 2:
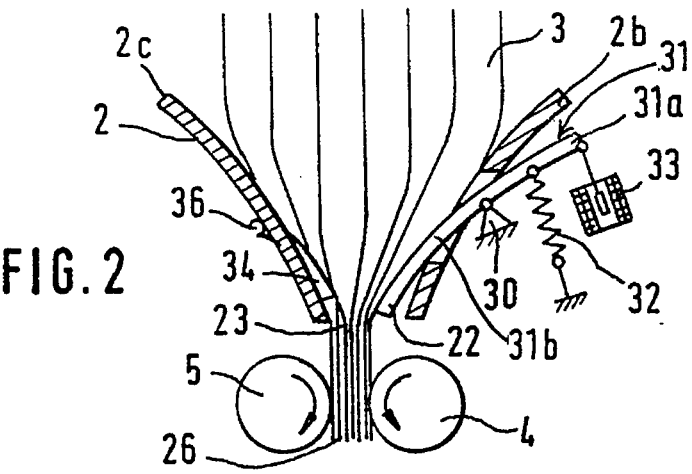
FIG. 2 is a sectional top plan view of the component illustrated in FIG. 1b, showing further details.

FIG. 2 shows how the individual slivers 3 are brought together by the sliver guiding device 2 to assume therein a side-by-side contacting relationship to form the sliver assembly and how they are sensed in the constriction 23 by means of the sensor element 22. The sensor element 22 has a lever arm 31a which is exposed to the pulling force of a tension spring 32 and is coupled with a measuring element 33 which may be a plunger-and-solenoid arrangement. Another lever arm 31b laterally continuously engages with its free end the sliver assembly formed of slivers 3. Thickness changes in the throughgoing fiber quantities of the slivers 3 are thus sensed as volume changes. Departing from FIG. 1b, the withdrawing rollers 4 and 5 are arranged vertically, that is, the slivers are laterally clamped by the nip 26 of the rollers 4 and 5.

Figure 3A:
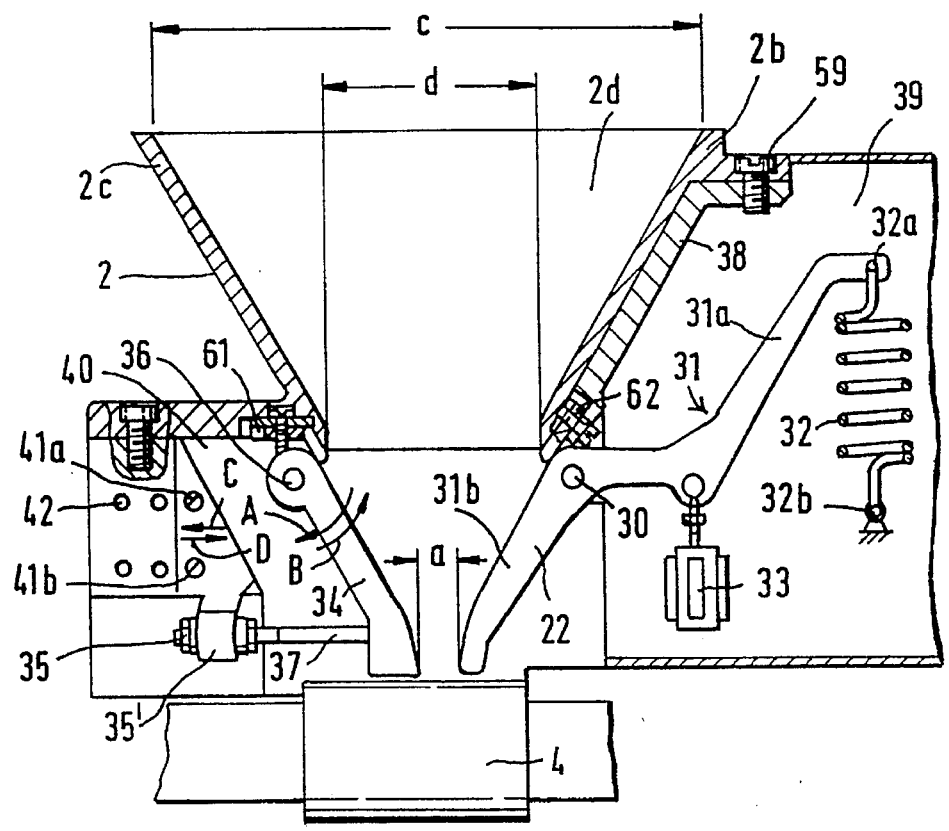
FIG. 3a is a sectional top plan view of a preferred embodiment, showing structural details and illustrating the construction in a first setting.
Figure 3B:
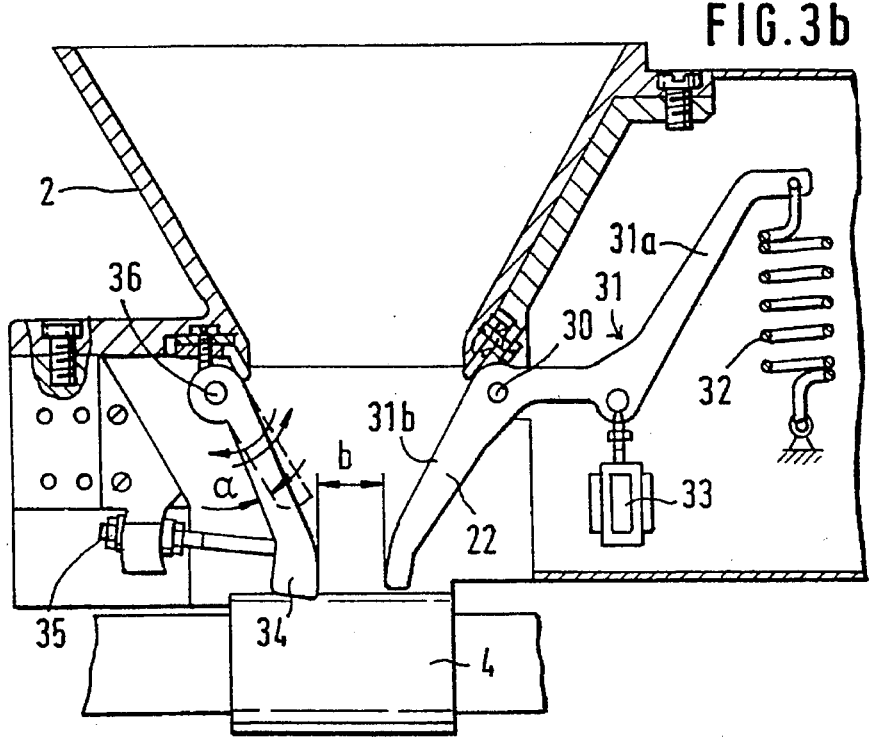
FIG. 3b is a view similar to FIG. 3a, illustrating the construction in a second setting.
Figure 5:
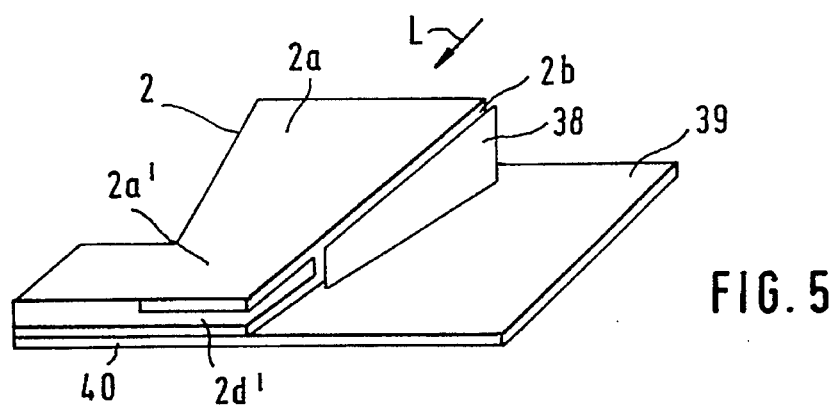
FIG. 5 is a perspective view of a sliver guiding device according to a preferred embodiment of the invention.

FIGS. 3a, 3b and 5 show the apparatus for measuring the thickness of a sliver assembly formed of slivers 3. The guiding device 2 has four walls 2a, 2b, 2c and 2d, of which at least two oppositely located walls converge towards one another in the downstream direction, that is, in the sliver advancing direction L. The walls 2a–2d cause the slivers 3 to converge and assume a side-by-side position in a single plane to form the sliver assembly. As the sliver assembly exits from the device 2, it enters the withdrawing rollers 4 and 5 after which the sliver assembly is dissolved as the individual slivers 3 assume a divergent course. In the downstream zone of the sliver guiding device the pivotal sensor element 22 is arranged which, together with the facing counterelement 34 forms the constriction 23 for the sliver assembly. The change in position of the sensor element 22 caused by a thickness variation of the sliver assembly applies mechanical signals to a transducer 33 which, accordingly, emits electric control pulses.

The counterelement 34 is pivotal in the direction of the arrows A, B about the axis of a rotary bearing (pivot pin) 36 parallel to the plane in which the slivers 3 are arranged side-by-side. The rotary bearing 36 is arranged at the outlet end of the guide wall 2c, as best seen in FIG. 3a. The counterelement 34 may be adjusted and immobilized in the adjusted position, for example, by a setscrew 35 having a stem 37 engaging the counterelement 34 at a location spaced from the pivot pin 36. The setscrew 35 is held in a support bracket 35'. The support bracket 35' and the rotary bearing 36 are secured in threaded bores 42 in a base plate 40 by means of screws 41a, 41b, and are laterally shiftable to new adjusted positions as indicated by the arrows C and D. The sensor element 22 and the counterelement 34 project through the lateral walls 2b and 2c. By means of the setscrew 35 the counterelement 34 is rotated about the rotary axis 36, for example, when the processed sliver type is changed (the drawing frame 1 is inoperative during such changing operation), so that the distance between the counterelement 34 and the sensor element 22 is, in the constriction 23, changed from the distance a (FIG. 3a) to the distance b (FIG. 3b). At the same time, the angle α between the wall 2c and the counterelement 34 is also changed. The sensor element 22 biased by the spring 32 engaging the lever arm 31a of the sensor element 22 reacts to all changes of thicknesses of the throughgoing slivers 3, as a result of which the distance between the sliver engaging tip of the sensor element 22 and the finely adjusted counterelement 34 varies as a function of the thickness fluctuations.

As seen in FIG. 3a, the sliver guiding device 2 has two opposite, converging side walls 2b, 2c having an inlet width c and an outlet width d. The side wall 2b lies with its outer face against a web-like holding element (engagement plate) 38 which, as best shown in FIG. 5, is secured to a base plate 39. The sliver guiding device 2 is secured to the holding element 38 by a screw 59. The holding element 38 extends perpendicularly to the base plate 39 and parallel to the side wall 2b.

Figure 4:
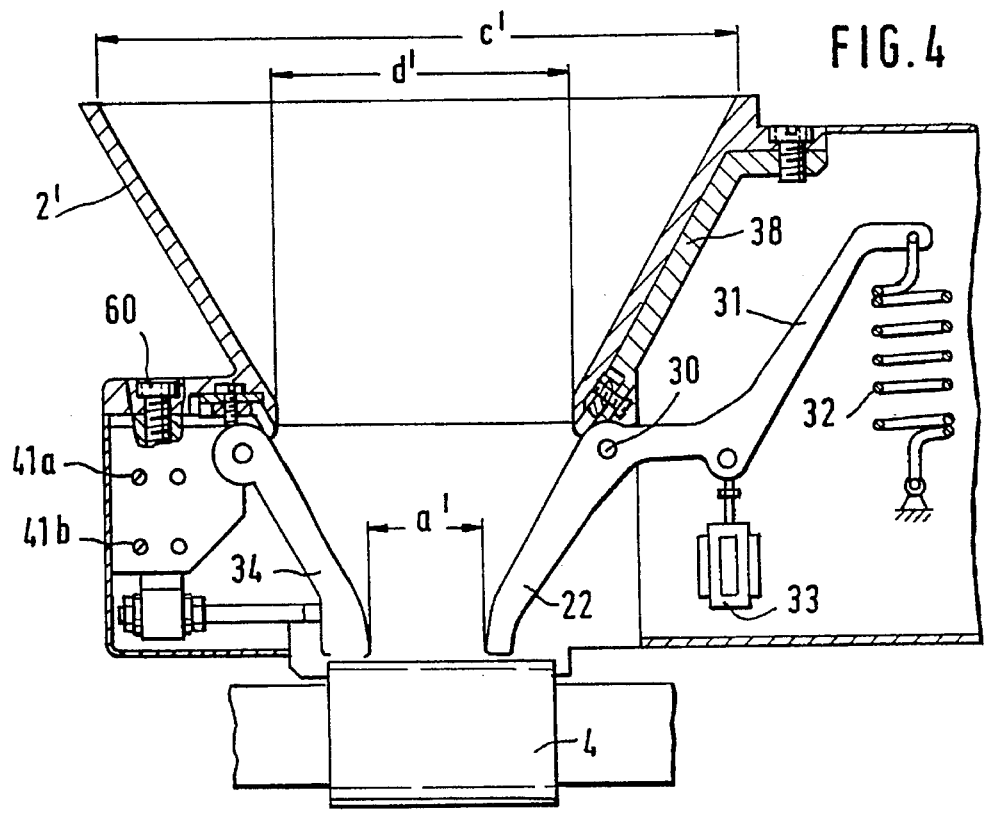
FIG. 4 is a sectional top plan view of a preferred embodiment, showing structural details and illustrating the construction in a third setting by virtue of component replacement.
Figure 4A:
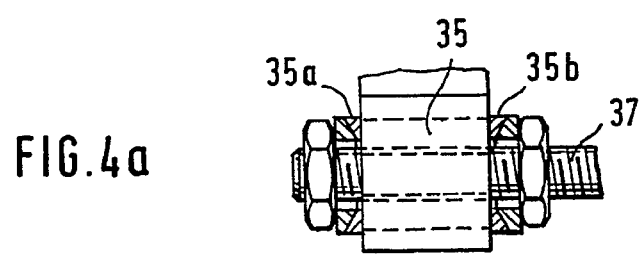

In the construction shown in FIG. 4, the sliver guiding device 2 of the earlier described embodiment is replaced by a sliver guiding device 2' having a greater inlet width c' and a greater outlet width d' than the respective dimensions c and d of the sliver guiding device 2. The converging walls of the sliver guiding device 2' are inclined at a different angle than in the sliver guiding device 2. As an alternative, it may be feasible to nest a smaller sliver guiding device in a permanently attached sliver guiding device of larger dimensions. A replacement of a sliver guiding device 2' for a sliver guiding device 2 is effected, for example, because of a change in the type of the sliver to be processed by the drawing frame.

Reverting to FIG. 5, the guide wall 2a in the zone of the constriction 23, that is, in the zone of the outlet of the sliver guiding device 2 for the fiber slivers 3, has a zone 2a' which faces a zone 2d' of the guide wall 2d. The lateral walls 2b and 2c include a slot in the zone of the constriction 23 so that the sensor element 22 and the counterelement 34 may project therethrough and may engage, under pressure, laterally opposite sides of the sliver assembly composed of the side-by-side arranged slivers 3. The base surface 2d' merges into the base plates 39 and 40 situated externally of the sliver guiding device 2.

Turning to FIGS. 6a and 6b, the sensor element 22 is a lever pivotal about the bearing 30 and has lever arms 31a and 31b extending in opposite directions from the bearing 30. The lever 31 is swingable as indicated by the arrows E and F. At the end of the lever arm 31a, the sensor element 22 is engaged by a tension spring 32, whose other end is secured to a single-arm adjusting lever 43 which is rotatable about a pivot 44 in the direction of the arrows G and H. The free outer end of the lever 43 may form a manually engageable handle. The pivot 44 is secured to the base plate 39. In case the setting lever—which may be immobilized by detents—is moved from its position shown in FIG. 6a in the direction of the arrow H into the position shown in FIG. 6b, the securing location of the spring 32 is changed, whereby the bias and thus the spring force exerted on the sensor element 22 is altered. The base plate 39 has detents 45 and 46 such as slots and bolts for determining positions for the setting lever 43.

Figure 7A:
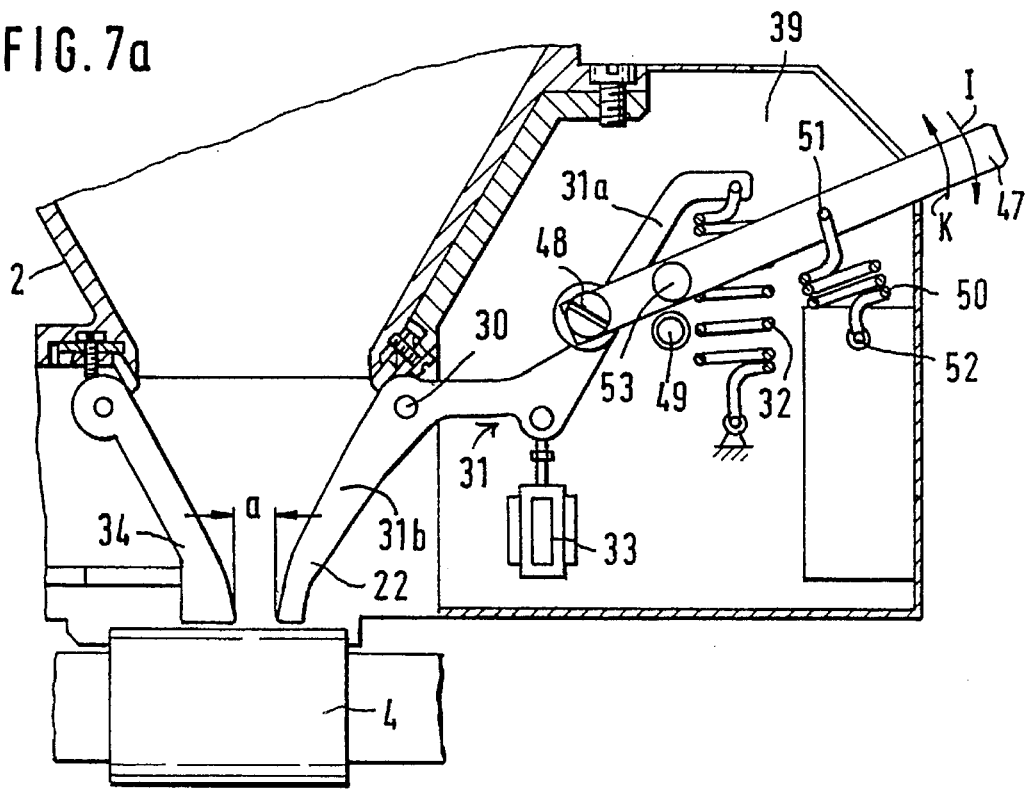
FIGS. 7a and 7b are sectional top plan views of yet another preferred structural embodiment of the invention, showing two operational positions.
Figure 7B:
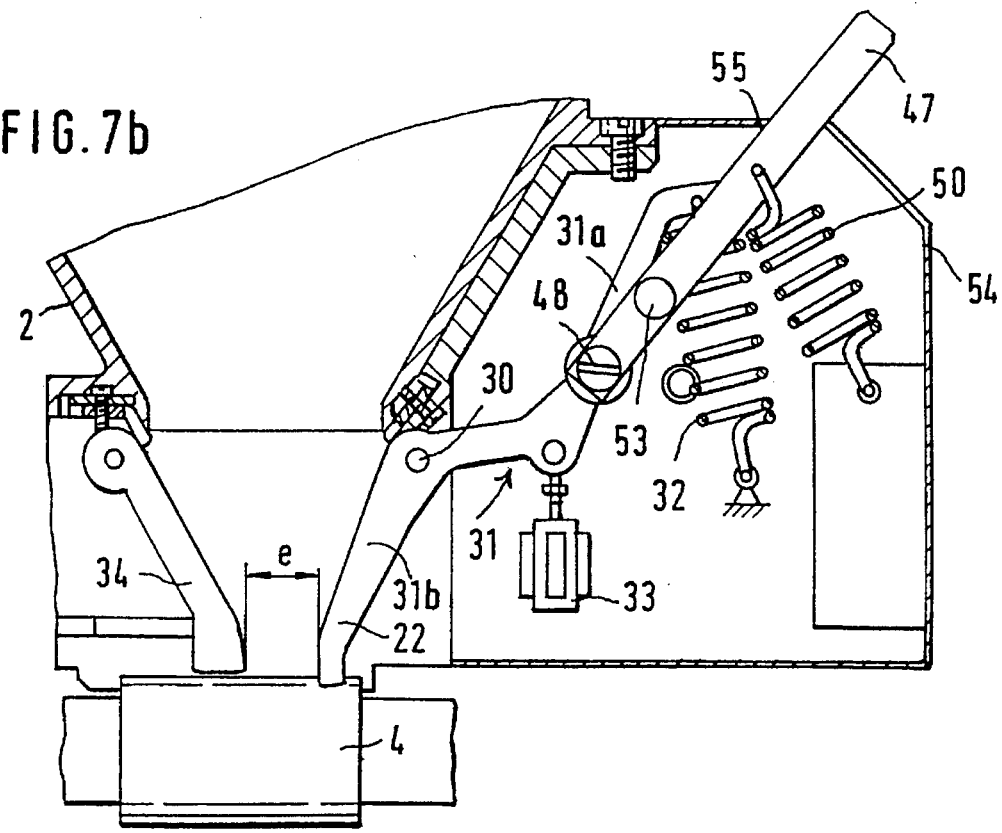

FIGS. 7a and 7b show a single-arm pivotal lever 47 which is swingable in the direction of the arrows I and K about a pivot 48 secured to the base plate 39. One end of a tension spring 50 is connected to the pivotal lever 47 at a location 51, while the other end of the tension spring 50 is secured to a stationary spring support 52. On the pivot lever 47 a carrier element, for example, a pin 53 is provided which is connected with the lever arm 31a of the lever 31 forming the sensor element 22. In case the pivot lever 47 is moved from its position shown in FIG. 7a in the direction of the arrow I into the position shown in FIG. 7b, then by virtue of the pressure by the pin 53 the lever arm 31a is shifted, as a result of which the distance between the sensor element 22 and the counterelement 34 is increased from a (FIG. 7a) to e (FIG. 7b). In this manner, the opening in the zone of the fiber outlet is significantly increased to what may be termed as a servicing opening e. The servicing opening e facilitates a thread-in operation for the slivers 3 upon a start of operation or readily permits a cleaning of the inner surfaces of the sliver guiding device 2. The immobilizing or detent devices for the pivot lever 47 (such as wall apertures) are designated at 54 and 55.

Figure 8:
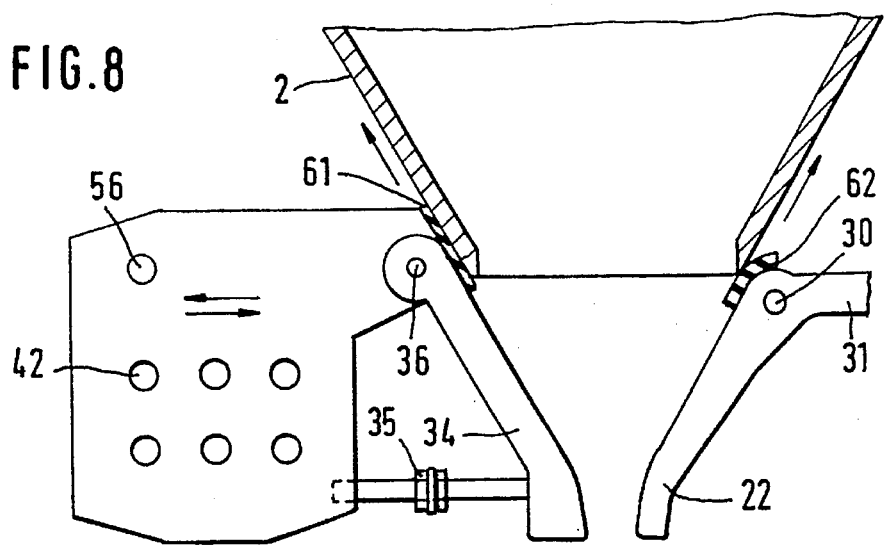
FIGS. 8, 9 and 10 are schematic sectional top plan views of three additional preferred embodiments of the invention.

In FIG. 8, the rotary bearing 36 supporting the counterelement 34 and the setting device including the setscrew 35 are mounted on a shifting element 56, whose position may be changed and which may be immobilized by screws received in threaded bore holes 42 of the base plate 40, as shown in FIG. 3a. Between the side walls 2b and 2c of the sliver guiding device 2 on the one hand and the sensor element 22 and the counterelement 34 on the other hand, respective rubber seals 62 and 61 are arranged, as also shown in FIG. 3a.

Figure 9:
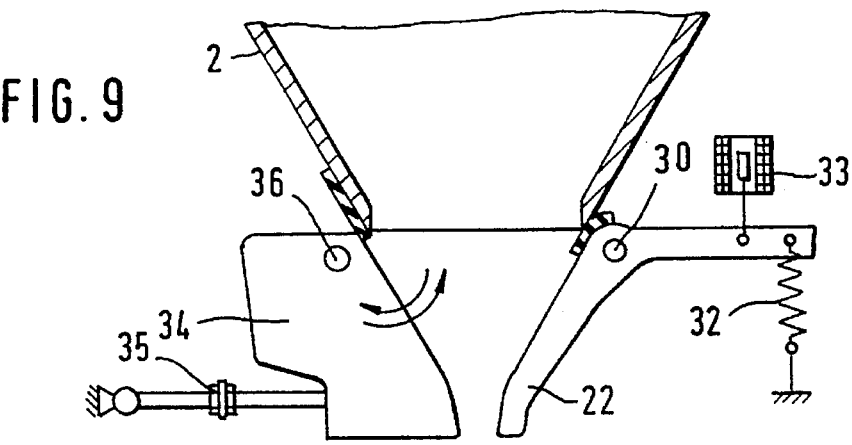

According to FIG. 9, the counterelement 34 is rotatably mounted on the bearing 36.

Figure 10:
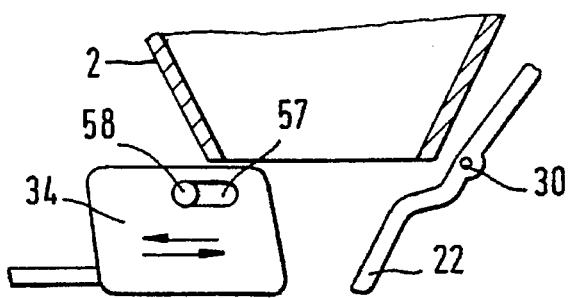

Turning to FIG. 10, the counterelement 34 is provided with a slot 57 through which a screw 58 extends. This arrangement provides for both a pivotal and a linear shifting motion of the counterelement 34. The screw 58, in addition to functioning as a pivot and a linear guide, also serves for immobilizing the counterelement 34 in its set position.

It will be understood that the above description of the present invention is susceptible to various modifications, changes and adaptations, and the same are intended to be comprehended within the meaning and range of equivalents of the appended claims.

What is claimed is:

1. An apparatus kit for measuring sliver thickness in a drawing frame, comprising
   (a) first and second sliver guiding devices, each including
      (1) an inlet opening for simultaneously receiving a plurality of side-by-side running slivers having an advancing direction; said inlet opening having a cross-sectional sliver passage area;
      (2) sliver combining means defining a plane extending parallel to said advancing direction for bringing the slivers together to form a sliver assembly constituted by a plurality of side-by-side positioned running slivers arranged in said plane and laterally contacting one another; the sliver assembly having oppositely located first and second outermost slivers; said sliver combining means comprising oppositely located, converging wall surfaces;
      (3) an outlet opening for discharging the sliver assembly; said outlet opening having a cross-sectional sliver passage area; at least one of said cross-sectional sliver passage areas of said first sliver guiding device being different from a respective said cross-sectional sliver passage area of said second sliver guiding device;
   (b) receiving means for receiving a selected one of said first and second sliver guiding devices;
   (b) a sensor element contacting said first outermost sliver at said outlet;
   (c) positioning means for movably supporting said sensor element;
   (d) a counterelement contacting said second outermost sliver at said outlet opening of said selected sliver guiding device;
   (g) biasing means for urging said sensor element into a resilient contact with said first outermost sliver in a direction towards said second outermost sliver, whereby said sensor element undergoes excursions upon variation of thickness of said sliver assembly in said plane; said sensor element and said counterelement together defining a restriction through which said sliver assembly passes; said sensor element and said counterelement forming part of said combining means of said selected sliver guiding device;
   (h) transducer means for converting excursions of said sensor member into electric pulses;
   (i) a withdrawing roller pair supported downstream of said selected sliver guiding device as viewed in said advancing direction; said withdrawing roller pair defining a nip through which the sliver assembly passes; and
   (j) means for driving said withdrawing roller pair for pulling said sliver assembly through said selected sliver guiding device.

2. The apparatus kit as defined in claim 1, wherein said receiving means includes means for releasably accommodating the selected said sliver guiding device.

3. The apparatus kit as defined in claim 2, wherein said receiving means comprises an engagement plate for contacting face-to-face an outer surface of the selected sliver guiding device.

4. The apparatus kit as defined in claim 1, wherein said first sliver guiding device is comprised in said receiving means and further wherein said second sliver guiding device is nestingly received in said first sliver guiding device when said second sliver guiding device is the selected sliver guiding device.

* * * * *